United States Patent
Heidecke et al.

(10) Patent No.: US 8,846,324 B2
(45) Date of Patent: Sep. 30, 2014

(54) IN VITRO METHOD FOR DIAGNOSING OR PREDICTING HYPERTENSION AND/OR EARLY-STAGE CARDIOVASCULAR END-ORGAN DAMAGE BY DETERMINING THE CONCENTRATION OF SOLUBLE PRORENIN RECEPTOR

(75) Inventors: Harald Heidecke, Berlin (DE); Kai Schulze-Forster, Teltow (DE)

(73) Assignee: CellTrend GmbH, Luckenwalde (DE)

(*) Notice: Subject to any disclaimer, the term of this patent is extended or adjusted under 35 U.S.C. 154(b) by 0 days.

(21) Appl. No.: 13/878,244

(22) PCT Filed: Sep. 22, 2011

(86) PCT No.: PCT/EP2011/066494
§ 371 (c)(1),
(2), (4) Date: Jun. 24, 2013

(87) PCT Pub. No.: WO2012/045587
PCT Pub. Date: Apr. 12, 2012

(65) Prior Publication Data
US 2013/0266974 A1 Oct. 10, 2013

(30) Foreign Application Priority Data
Oct. 6, 2010 (EP) .................................. 10186758

(51) Int. Cl.
*G01N 33/53* (2006.01)
*G01N 33/567* (2006.01)
*G01N 33/566* (2006.01)
*C07K 16/00* (2006.01)
*C12P 21/08* (2006.01)
*G01N 33/68* (2006.01)
*C07K 16/28* (2006.01)

(52) U.S. Cl.
CPC ........ *G01N 33/6887* (2013.01); *G01N 2800/32* (2013.01); *G01N 2333/705* (2013.01); *G01N 33/6893* (2013.01); *C07K 16/28* (2013.01); *C07K 16/2869* (2013.01); *G01N 2800/322* (2013.01)

USPC .................. 435/7.2; 436/501; 530/387.9

(58) Field of Classification Search
CPC ..... G01N 33/52; G01N 33/53; G01N 33/537; G01N 2333/705; G01N 2800/32; G01N 2800/347; G01N 2800/368; C07K 16/28; C07K 16/2869

See application file for complete search history.

(56) References Cited

U.S. PATENT DOCUMENTS

2010/0196367 A1 8/2010 Day
2011/0190142 A1* 8/2011 Funke-Kaiser et al. .......... 506/7

FOREIGN PATENT DOCUMENTS

WO WO 2009/143619 12/2009

OTHER PUBLICATIONS

Cousin et al., "Soluble form of the (pro)renin receptor generated by intracellular cleavage by furin is secreted in plasma", *Hypertension*, 53(6):1077-1082, 2009.
Gonzalez et al., "Soluble form of the (pro)renin receptor is augmented in the collecting duct and urine of chronic angiotensin II-dependent hypertensive rats", *Hypertension*, 57(4):859-864, 2011.
Nguyen et al., "Pivotal role of the renin/prorenin receptor in angiotensin II production and cellular responses to renin", *J Clin Invest.*, 109(11):1417-27, 2002.
PCT International Preliminary Report on Patentability issued in International Application No. PCT.EP2011/066494, issued Apr. 9, 2013.
PCT International Search Report and Written Opinion issued in International Application No. PCT.EP2011/066494, mailed Feb. 24, 2012.

* cited by examiner

*Primary Examiner* — Robert Landsman
(74) *Attorney, Agent, or Firm* — Parker Highlander PLLC

(57) ABSTRACT

A method for diagnosis and/or prediction of hypertension and/or cardiovascular end-organ damage is disclosed. The method disclosed comprises the determination of the presence of soluble pro-renin receptor in samples derived from a subject. Furthermore, the use of anti-sPRR antibodies in diagnosis and/or prediction of cardiovascular end-organ damage is encompassed.

18 Claims, 10 Drawing Sheets

Fig. 1

Figure 2:
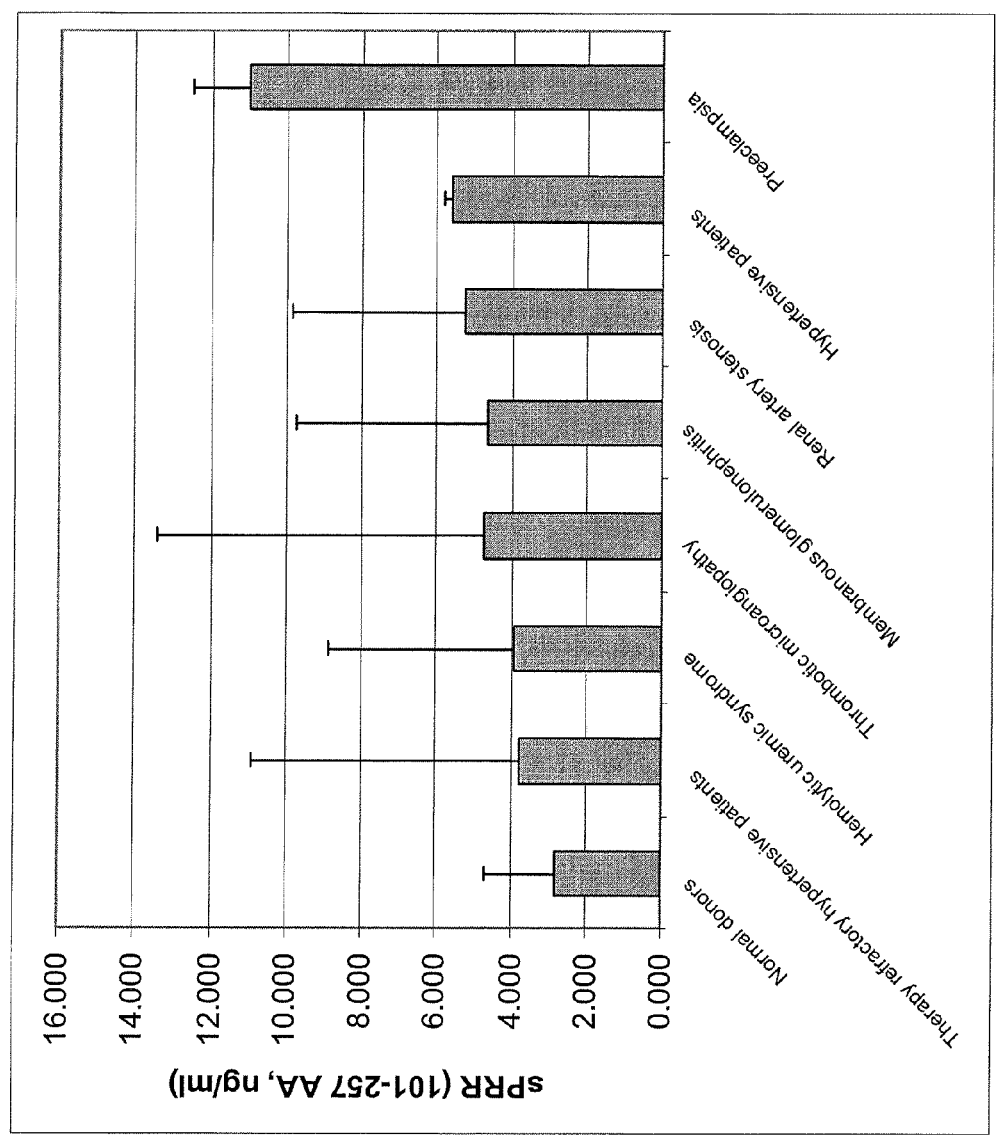

```
  1    mavfvvllal   vagvlgnefs   ilkspgsvvf   rngnwpipge   ripdvaalsm
       gfsvkedlsw
 61    pglavgnlfh   rpratvmvmv   kgvnklalpp   gsvisyplen   avpfsldsva
       nsihslfsee
121    tpvvlqlaps   eervymvgka   nsvfedlsvt   lrqlrnrlfq   ensvlsslpl
       nslsrnnevd
181    llflselqvl   hdissllsrh   khlakdhspd   lyslelagld   eigkrygeds
       eqfrdaskil
241    vdalqkfadd   myslyggnav   velvtvksfd   tslirktrti   leakqaknpa
       spynlaykyn
301    feysvvfnmv   lwimialala   viitsyniwn   mdpgydsiiy   rmtnqkirmd
```

IN VITRO METHOD FOR DIAGNOSING OR PREDICTING HYPERTENSION AND/OR EARLY-STAGE CARDIOVASCULAR END-ORGAN DAMAGE BY DETERMINING THE CONCENTRATION OF SOLUBLE PRORENIN RECEPTOR

CROSS-REFERENCE TO RELATED APPLICATION

This application is a national phase application under 35 U.S.C. § 371 of International Application No. PCT/EP2011/066494, filed on Sep. 22, 2011 which claims priority to European Patent Application No. 10186758.8 filed on Oct. 6, 2010 the entire contents and disclosures of which are specifically incorporated by reference herein without disclaimer.

FIELD OF THE INVENTION

The present invention is in the filed of biology and chemistry, more in particular immunology as well as diagnostics and therapeutics, more in particular in the field of diagnosis of pulmonary arterial hypertension, scleroderma, cancer, cardiomyopathies and pre-eclampsia.

BACKGROUND OF THE INVENTION

Arterial hypertension is one of the most important risk factors for cardiovascular morbidity and mortality. Recent epidemiological analyses show that the prevalence of arterial hypertension increases dramatically in Germany and also world-wide. The clinical importance of arterial hypertension is associated with resulting in cardiovascular end-organ damages. About 90-95% of the patients suffering from hypertension have a so called "primary hypertension", which refers to high blood pressure for which no medical cause can be found (Carretero O A, Oparil S (January 2000), "Essential hypertension. Part I: definition and etiology", Circulation 101 (3): 329-35). In the remaining 5-10% of the cases hypertension is caused by other conditions that affect kidneys, arteries, heart, or the endocrine system. These patients suffer from a so called "secondary hypertension" (Pierdomenico S D, Di Nicola M, Esposito A L, et al. (June 2009), "Prognostic Value of Different Indices of Blood Pressure Variability in Hypertensive Patients", American Journal of Hypertension 22 (8): 842-7).

Regularly, hypertension is diagnosed on the basis of a persistently high blood pressure. Initial assessment of the hypertensive patient should include a complete history and physical examination. If the elevation is extreme or if symptoms of organ damage are present, treatment has to start immediately to prevent further damages.

After the diagnosis of hypertension, physicians will attempt to identify the underlying cause based on risk factors and other symptoms. Secondary hypertension, i.e. hypertension caused by other conditions is more common in preadolescent children. In most cases it is caused by a renal disease. Primary or essential hypertension is more common in adolescents and has multiple risk factors, including obesity and a family history of hypertension. Laboratory tests can also be performed to identify possible causes of secondary hypertension and determine if hypertension has caused damage to the heart, eyes, and kidneys.

Pre-eclampsia is a syndrome of hypertension, oedema, and proteinuria that affects 5 to 10% of pregnancies and results in substantial maternal and fetal morbidity and mortality. Pre-eclampsia accounts for at least 200,000 maternal deaths worldwide per year. The symptoms of pre-eclampsia typically appear after the $20^{th}$ week of pregnancy and are usually detected by routine monitoring of the woman's blood pressure and urine. However, these monitoring methods are ineffective for diagnosis of the syndrome at an early stage. Such early detection could reduce the risk for the subject or developing fetus, if an effective treatment were available. Currently there are no known cures for pre-eclampsia. Pre-eclampsia can vary in severity from mild to life-threatening. A mild form of pre-eclampsia can be treated with bed rest and frequent monitoring. For moderate to severe cases, hospitalization is required and blood pressure medication or anticonvulsant medications to prevent seizures are administered. If the condition becomes life-threatening to the mother or the baby the pregnancy is terminated and the baby is delivered pre-term.

Fifteen years ago, a panel of experts representing the full spectrum of cardiovascular disease (CVD) research and practice assembled at a workshop to examine the state of knowledge about CVD. The leaders of the workshop generated a hypothesis that framed CVD as a chain of events, initiated by a myriad of related and unrelated risk factors and progressing through numerous physiological pathways and processes to the development of end-stage heart disease; see FIG. 10 They further hypothesized that intervention anywhere along the chain of events leading to CVD could disrupt the pathophysiological process and confer cardioprotection. The workshop participants endorsed this paradigm but also identified the unresolved issues relating to the concept of a CVD continuum. There was limited availability of clinical trial data and pathobiological evidence at that time, and the experts recognized that critical studies at both the mechanistic level and the clinical level were needed to validate the concept of a chain of events leading to end-stage CVD.

In the intervening 15 years, new evidence for underlying pathophysiological mechanisms, the development of novel therapeutic agents, and the release of additional landmark clinical trial data have confirmed the concept of a CVD continuum and reinforced the notion that intervention at any point along this chain can modify CVD progression. In addition, the accumulated evidence indicates that the events leading to disease progression overlap and intertwine and do not always occur as a sequence of discrete, tandem incidents. Furthermore, although the original concept focused on risk factors for coronary artery disease (CAD) and its sequelae, the CVD continuum has expanded to include other areas such as cerebrovascular disease, peripheral vascular disease, and renal disease. Since its conception 15 years ago, the CVD continuum has become much in need of an update.

The recently described prorenin receptor (PRR) is a new trans-membrane receptor that binds both renin and prorenin. This binding increases the catalytic activity of renin four to five fold, activates prorenin nonproteolytically and induces the activation of MAP-kinase ERK½. The extracellular part is cleaved after amino acid 277. However, its function has not been fully understood yet.

However, so far, all known tests are restricted to one or few caused cardiovascular end-organ damages or conditions causing hypertension. Thus, there is a need for a reliable method to diagnose hypertension and/or cardiovascular end-organ damage. The problem underlying the present invention, therefore, may in one aspect be seen in the provision of a method for the diagnosis of hypertension and/or cardiovascular end-organ damage.

The inventors have unexpectedly found that the presence of soluble PRR (sPRR; SEQ ID NO. 2) in samples of subjects are indicative for the presence of hypertension and/or cardiovascular end-organ damage as well other disease states of the CVD continuum.

So far it was not possible to detect sPRR in samples of subjects using standard ELISA. The inventors now unexpectedly found that an antibodies specifically binding to the amino acid sequence of SEQ ID NO. 4 are well suited for the detection of sPRR in samples of subjects. By that the inventors provide an antibody which allows the detection of sPRR and contributes to the solution of the above mentioned problems.

DESCRIPTION OF THE INVENTION

The present invention provides a solution for the above-mentioned problem. The solution comprises an in vitro method for diagnosis or prediction of hypertension and/or early stage cardiovascular end-organ damage, wherein the presence of soluble prorenin receptor (sPRR) or fragments thereof is determined in a sample from a patient to be diagnosed, wherein the presence of sPRR or fragments thereof at increased concentration compared to the concentration of sPRR in samples from healthy subjects is indicative for hypertension and/or early stage cardiovascular end-organ damage and wherein the presence of SPRR or fragments thereof at decreased concentration compared to the concentration of SPRR in samples from healthy subjects is indicative for late stage cardiovascular end-organ damage.

The solution comprises an in vitro method for diagnosis or prediction of hypertension and/or cardiovascular end-organ damage, wherein the concentration of sPRR or fragments thereof is determined in a sample from a patient to be diagnosed, and wherein the concentration of sPRR or fragments thereof is compared to concentration of sPRR in samples from healthy subjects, wherein an increased concentration of sPRR in the sample of the patient is indicative for hypertension and/or cardiovascular end-organ damage.

The invention also pertains to a method for diagnosing the presence of hypertension and/or cardiovascular diseases or other disease states of the CVD continuum in a subject or predicting the risk of a subject for contracting hypertension and/or cardiovascular end-organ disease or for identifying a subject having an enhanced risk for contracting hypertension and/or cardiovascular end-organ disease in a subject as described above, wherein the concentration of sPRR or fragments thereof, either alone or in conjunction with other prognostically useful laboratory or clinical parameters, is used for diagnosing the presence of hypertension and/or cardiovascular diseases in a subject or prediction of the risk of a subject for contracting hypertension and/or cardiovascular end-organ disease or for the diagnosis of hypertension and/or cardiovascular end-organ disease by a method which may be selected from the following alternatives:
- comparison with the median of the concentration of sPRR or fragments thereof in an ensemble of pre-determined samples in a population of apparently healthy subjects,
- comparison with a quantile of the concentration of sPRR or fragments thereof in an ensemble of pre-determined samples in a population of apparently healthy subjects,
- calculation based on Cox Proportional Hazards analysis or by using risk index calculations such as the NRI (Net Reclassification Index) or the IDI (Integrated Discrimination Index).

In a preferred embodiment of the methods according to the present invention the concentration of a polypeptide comprising an amino acid sequence is selected from the group consisting of SEQ ID NO. 2, SEQ ID NO. 3, and SEQ ID NO. 4, or fragments thereof. In a further preferred embodiment of the present invention, the concentration of an polypeptide comprising the amino acid sequence of position 1 to 302 of sPRR is determined, preferably the concentration of a polypeptide comprising the amino acid sequence of position 1 to 277 of sPRR is determined, even more preferably the concentration of a polypeptide comprising the amino acid sequence of 101 to 257 of sPRR is determined.

In one embodiment of the present invention the determined fragments of sPRR have a length of at least 6 amino acids, preferably at least 10 amino acids, more preferably at least 20 amino acids, even more preferably at least 100 amino acids.

In the present invention the term "prediction" denotes a prognosis of how a subject's (e.g. a patient's) medical condition will progress. This may include an estimation of the chance of recovery or the chance of an adverse outcome for said subject, e.g. a cardiovascular end-organ damage and/or hypertension.

In one embodiment of the present invention the presence of sPRR or a fragment thereof over or under a certain threshold is indicative for the disease. The skilled person can calculate these thresholds using standard statistical methods, e.g. Receiver Operating Characteristic analysis (ROC analysis) or by determining the median or mean or a desired percentile.

The invention may also involve comparing the level or concentration of a marker (here sPRR or fragments thereof) for the individual with a predetermined value. The predetermined value can take a variety of forms. It can be single cut-off value, such as for instance a median or mean or the 75th, 90th, 95th or 99th percentile of a population. It can be established based upon comparative groups, such as where the risk in one defined group is double the risk in another defined group. It can be a range, for example, where the tested population is divided equally (or unequally) into groups, such as a low-risk group, a medium-risk group and a high-risk group, or into quartiles, the lowest quartile being individuals with the lowest risk and the highest quartile being individuals with the highest risk.

The predetermined value can vary among particular populations selected, depending on their habits, ethnicity, genetics etc. For example, an apparently healthy, non-smoker population (no detectable disease, particularly no hypertension and/or cardiovascular end-organ disease) might have a different 'normal' range of markers than a smoking population or a population whose members have hypertension and/or cardiovascular end-organ disease. Accordingly, the predetermined values selected may take into account the category in which an individual falls. Appropriate ranges and categories can be selected with no more than routine experimentation by those of ordinary skill in the art.

In a specific embodiment of the method according to the invention the use of said concentration of sPRR or fragments thereof comprises comparing said concentration of sPRR or fragments thereof to a threshold concentration, whereby, when said level of sPRR or fragments thereof exceeds said threshold concentration, hypertension and/or cardiovascular end-organ damage is diagnosed and/or predicted in a subject.

Other preferred cut-off values are for instance the 90th, 95th or 99th percentile of a normal population. By using a higher percentile than the 75th percentile, one reduces the number of false positive subjects identified, but one might miss to identify subjects, who are at moderate, albeit still increased risk. Thus, one might adopt the cut-off value depending on whether it is considered more appropriate to identify most of the subjects at risk at the expense of also identifying "false positives", or whether it is considered more appropriate to identify mainly the subjects at high risk at the expense of missing several subjects at moderate risk.

Other mathematical possibilities to calculate an individual's risk by using the individual's sPRR concentration and other prognostic laboratory and clinical parameters are for instance based on Cox regression analysis or are the NRI (Net Reclassification Index) or the IDI (Integrated Discrimination Index). The indices can be calculated according to Pencina (Pencina M J, et al.: Evaluating the added predictive ability of a new marker: from area under the ROC curve to reclassification and beyond. Stat Med. 2008; 27:157-172).

The sensitivity and specificity of a diagnostic and/or prognostic test depends on more than just the analytical "quality" of the test, they also depend on the definition of what constitutes an abnormal result. In practice, Receiver Operating Characteristic curves (ROC curves) are typically calculated by plotting the value of a variable versus its relative frequency in "normal" (i.e. apparently healthy) and "disease" populations (i.e. patients suffering from bacterial infections). For any particular marker, a distribution of marker levels for subjects with and without a disease will likely overlap. Under such conditions, a test does not absolutely distinguish normal from disease with 100% accuracy, and the area of overlap indicates where the test cannot distinguish normal from disease. A threshold is selected, above which (or below which, depending on how a marker changes with the disease) the test is considered to be abnormal and below which the test is considered to be normal. The area under the ROC curve is a measure of the probability that the perceived measurement will allow correct identification of a condition. ROC curves can be used even when test results do not necessarily give an accurate number. As long as one can rank results, one can create a ROC curve. For example, results of a test on "disease" samples might be ranked according to degree (e.g. 1=low, 2=normal, and 3=high). This ranking can be correlated to results in the "normal" population and a ROC curve created. These methods are well known in the art (Hanley et al. 1982. Radiology 143: 29-36). Preferably, a threshold is selected to provide a ROC curve area of greater than about 0.5, more preferably greater than about 0.7, still more preferably greater than about 0.8, even more preferably greater than about 0.85, and most preferably greater than about 0.9. The term "about" in this context refers to +/−5% of a given measurement.

The horizontal axis of the ROC curve represents (1−specificity), which increases with the rate of false positives. The vertical axis of the curve represents sensitivity, which increases with the rate of true positives. Thus, for a particular cut-off selected, the value of (1−specificity) may be determined, and a corresponding sensitivity may be obtained. The area under the ROC curve is a measure of the probability that the measured marker level will allow correct identification of a disease or condition. Thus, the area under the ROC curve can be used to determine the effectiveness of the test.

As described herein after, a panel response value is preferably determined by plotting ROC curves for the sensitivity of a particular panel of markers versus 1−(specificity) for the panel at various cut-offs. In these methods, a profile of marker measurements from a subject is considered together to provide a global probability (expressed either as a numeric score or as a percentage risk) of a diagnosis or prognosis. In such embodiments, an increase in a certain subset of markers may be sufficient to indicate a particular diagnosis/prognosis in one patient, while an increase or decrease in a different subset of markers may be sufficient to indicate the same or a different diagnosis/prognosis in another patient. Weighting factors may also be applied to one or more markers in a panel, for example, when a marker is of particularly high utility in identifying a particular diagnosis/prognosis, it may be weighted, so that at a given level, it alone is sufficient to signal a positive result. Likewise, a weighting factor may provide that no given level or concentration of a particular marker is sufficient to signal a positive result, but only signals a result when another marker also contributes to the analysis.

In certain embodiments, markers and/or marker panels are selected to exhibit at least about 70% sensitivity, more preferably at least about 80% sensitivity, even more preferably at least about 85% sensitivity, still more preferably at least about 90% sensitivity, and most preferably at least about 95% sensitivity, combined with at least about 70% specificity, more preferably at least about 80% specificity, even more preferably at least about 85% specificity, still more preferably at least about 90% specificity, and most preferably at least about 95% specificity. In particularly preferred embodiments, both the sensitivity and specificity are at least about 75%, more preferably at least about 80%, even more preferably at least about 85%, still more preferably at least about 90%, and most preferably at least about 95%. The term "about" in this context refers to +/−5% of a given measurement.

In other embodiments, a positive likelihood ratio, negative likelihood ratio, odds ratio, or hazard ratio is used as a measure of a test's ability to predict risk or diagnose a disease. In the case of a positive likelihood ratio, a value of 1 indicates that a positive result is equally likely among subjects in both the "diseased" and "control" groups; a value greater than 1 indicates that a positive result is more likely in the diseased group; and a value less than 1 indicates that a positive result is more likely in the control group. In the case of a negative likelihood ratio, a value of 1 indicates that a negative result is equally likely among subjects in both the "diseased" and "control" groups; a value greater than 1 indicates that a negative result is more likely in the test group; and a value less than 1 indicates that a negative result is more likely in the control group. In certain preferred embodiments markers are preferably selected to exhibit a positive or negative likelihood ratio of at least about 1.5 or more or about 0.67 or less, more preferably at least about 2 or more or about 0.5 or less, still more preferably at least about 5 or more or about 0.2 or less, even more preferably at least about 10 or more or about 0.1 or less, and most preferably at least about 20 or more or about 0.05 or less. The term "about" in this context refers to +/−5% of a given measurement.

In the case of an odds ratio, a value of 1 indicates that a positive result is equally likely among subjects in both the "diseased" and "control" groups; a value greater than 1 indicates that a positive result is more likely in the diseased group; and a value less than 1 indicates that a positive result is more likely in the control group. In certain preferred embodiments, markers and/or marker panels are preferably selected to exhibit an odds ratio of at least about 2 or more or about 0.5 or less, more preferably at least about 3 or more or about 0.33 or less, still more preferably at least about 4 or more or about 0.25 or less, even more preferably at least about 5 or more or about 0.2 or less, and most preferably at least about 10 or more or about 0.1 or less. The term "about" in this context refers to +/−5% of a given measurement.

In the case of a hazard ratio, a value of 1 indicates that the relative risk of an endpoint (e.g., death) is equal in both the "diseased" and "control" groups; a value greater than 1 indicates that the risk is greater in the diseased group; and a value less than 1 indicates that the risk is greater in the control group. In certain preferred embodiments, markers and/or marker panels are preferably selected to exhibit a hazard ratio of at least about 1.1 or more or about 0.91 or less, more preferably at least about 1.25 or more or about 0.8 or less, still more preferably at least about 1.5 or more or about 0.67 or less, even more preferably at least about 2 or more or about 0.5 or less, and most preferably at least about 2.5 or more or about 0.4 or less. The term "about" in this context refers to +/5% of a given measurement.

The skilled artisan will understand that associating a diagnostic or prognostic indicator, with a diagnosis or with a prognostic risk of a future clinical outcome is a statistical analysis. For example, a marker level of greater than X may signal that a patient is more likely to suffer from an adverse outcome than patients with a level less than or equal to X, as determined by a level of statistical significance. Additionally, a change in marker concentration from baseline levels may be reflective of patient prognosis, and the degree of change in marker level may be related to the severity of adverse events. Statistical significance is often determined by comparing two or more populations, and determining a confidence interval and/or a p value. See, e.g., Dowdy and Wearden, Statistics for Research, John Wiley & Sons, New York, 1983. Preferred confidence intervals of the invention are 90%, 95%, 97.5%, 98%, 99%, 99.5%, 99.9% and 99.99%, while preferred p values are 0.1, 0.05, 0.025, 0.02, 0.01, 0.005, 0.001, and 0.0001.

In yet other embodiments, multiple determinations of diagnostic or prognostic markers can be made, and a temporal change in the marker can be used to determine a diagnosis or prognosis. For example, a marker concentration in a subject sample may be determined at an initial time, and again at a second time from a second subject sample. In such embodiments, an increase in the marker from the initial time to the second time may be indicative of a particular diagnosis, or a particular prognosis. Likewise, a decrease in the marker from the initial time to the second time may be indicative of a particular diagnosis, or a particular prognosis.

The inventors further found that concentrations of sPRR over a certain threshold in the samples of patients may be indicative and/or predictive for hypertension and/or cardiovascular end-organ damages. In one embodiment of the present invention a concentration of sPRR of at least 3 ng/ml is indicative of the disease, preferably a concentration of at least 4 ng/ml, more preferably a concentration of at least 5 ng/ml, even more preferably a concentration of at least 10 ng/ml.

The following values have been determined and may serve as possible cut-off values. It is important to understand that the genetic background of an individual may lead to a higher or lower value also in a healthy individual. Hence, the following values are preferably plus/minus 50%, plus/minus 40%, plus/minus 30%, plus/minus 25%, plus/minus 20%, plus/minus 15%, plus/minus 10%, plus/minus 5% or plus/minus 2.5%.

Healthy individual 1590 pg/ml sPRR

Healthy pregnant individual: 6500 pg/ml sPRR

Possible cut off values for:

Systolic heart failure (55 EF, lowered), dilative cardio myopathy (DCM) and kidney insufficiency (1.2 kreatinin, lower): 1260 pg/ml sPRR or lower Diabetes in pregnant individuals: 3750 pg/ml sPRR or lower Pre-eclampsia: 7000 pg/ml sPRR or higher The concentration of the markers as obtained by the methods or by the use of the assays according to the present invention may be analyzed in a number of fashions well known to a person skilled in the art. For example, each assay result obtained may be compared to a "normal" value, or a value indicating a particular disease or outcome. A particular diagnosis/prognosis may depend upon the comparison of each assay result to such a value, which may be referred to as a diagnostic or prognostic "threshold". In certain embodiments, assays for one or more diagnostic or prognostic indicators are correlated to a condition or disease by merely the presence or absence of the indicator(s) in the assay. For example, an assay can be designed so that a positive signal only occurs above a particular threshold concentration of interest, and below which concentration the assay provides no signal above background.

A "sample" in the meaning of the invention can be a biological fluid such as lymph, urine, cerebrospinal fluid, blood, serum, plasma, saliva. The sample is collected from the patient or subjected to the diagnosis according to the invention. In a preferred embodiment of the present invention the sample is selected from the group comprising a blood sample, a serum sample, and a plasma sample.

Where appropriate, the sample may need to be homogenized or extracted with a solvent prior to use in the present invention in order to obtain a liquid sample. A liquid sample hereby may be a solution or suspension.

Samples may be subjected to one or more pre-treatments prior to use in the present invention. Such pre-treatments include, but are not limited to, dilution, filtration, centrifugation, concentration, sedimentation, precipitation, and dialysis. In a preferred embodiment the sample is diluted two-fold with an appropriate buffer, preferably 10-fold, more preferably 20-fold, even more preferably the sample is diluted 25-fold with an appropriate buffer. Appropriate buffers for the dilution of the sample may be chosen by those skilled in the art. Preferred buffers do not interact with the binding of sRPP binding agents used in the method according to the present invention, e.g. antibodies or fragments thereof. Non-limiting examples of appropriate buffers is PBS-Casein buffer.

Pre-treatments may also include the addition of chemical or biochemical substances to the solution, such as acids, bases, buffers, salts, solvents, reactive dyes, detergents, emulsifiers, chelators.

The term "hypertension" refers to a condition where the pressure of blood within the blood vessels is higher than normal as it circulates through the body. When the systolic pressure exceeds 140 mmHg or the diastolic pressure exceeds 90 mmHg for a sustained period of time, damage is done to the body. Populations at increased risk due to other conditions, such as diabetes, are recommended to have even lower levels than cited above. Excessive systolic pressure can rupture blood vessels, and when it occurs within the brain, a stroke results. Hypertension may also cause thickening and narrowing of the blood vessels which ultimately could lead to atherosclerosis. The term "hypertension" as used herein is meant to encompass various types of hypertension, such as those described hereinafter, including primary hypertension, secondary hypertension, severe hypertension, pulmonary hypertension, malignant hypertension, and isolated systolic hypertension.

Early stage end-organ or target organ damage herein usually refers to damage occurring in major organs fed by the circulatory system (heart, kidneys, brain, eyes) which can sustain damage due to uncontrolled hypertension. Early stage cardiovascular end-organ damage includes left ventricular failure, unstable angina, myocardiacinfarction, encephalopathy, pre-eclampsia, eclampsia, cancer, secondary hypertension, e.g. therapy refractory hypertension, hemolytic uremic syndrome, thrombotic microangiopathy, membranous glomerulonephritis, and renal artery stenosis.

Late stage end-organ or target organ damage herein usually refers to damage occurring in major organs fed by the circulatory system (heart, kidneys, brain, eyes) such as systolic heart failure, dilative cardiomyopathy, kidney insufficiency and diabetes in pregnant female patients.

The term "pre-eclampsia" refers to the multi-system disorder that is characterized by hypertension with proteinuria or oedema, or both, glomerular dysfunction, brain oedema, liver oedema, or coagulation abnormalities due to pregnancy or the influence of a recent pregnancy. Pre-eclampsia generally occurs after the 20$^{th}$ week of gestation. Pre-eclampsia is generally defined as some combination of the following symptoms: (1) a systolic blood pressure (BP)>140 mmHg and a diastolic BP>90 mmHg after 20 weeks of gestation (generally measured on two occasions, 4-168 hours apart), (2) new onset proteinuria (1+ by dipstik on urn analysis, >300 mg of protein in a 24-hour urine collection, or a single random urine sample having a protein/creatinine ratio>0.3), and (3) resolution of hypertension and proteinuria by 12 weeks postpartum. Severe pre-eclampsia is generally defined as (1) a diastolic BP>110 mmHg (generally measured on two occasions, 4-168 hours apart) or (2) proteinuria characterized by a measurement of 3.5 g or more protein in a 24-hour urine collection or two random urine specimens with at least 3+ protein by dipstick, high pre-eclampsia, hypertension and proteinuria generally occur within seven days of each other. In severe pre-eclampsia, severe hypertension, severe proteinuria and HELLP syndrome (hemolysis, elevated liver enzymes, low platelets) or eclampsia can occur simultaneously or only one symptom at a time. Occasionally, severe pre-eclampsia can lead to the development of seizures. This severe form of the syndrome is referred to as "eclampsia." Eclampsia can also include dysfunction or damage to several organs or tissues such as the liver (e.g., hepatocellular damage, periportal necrosis) and the central nervous system (e.g., cerebral oedema and cerebral hemorrhage). The etiology of the seizures is thought to be secondary to the development of cerebral oedema and focal spasm of small blood vessels in the kidney.

"Cancer" herein relates to malignant neoplasia. Examples of malignant neoplasia include solid and haematological tumors. Solid tumors are exemplified by tumors of the breast, bladder, bone, brain, central and peripheral nervous system, colon, endocrine glands (e.g. thyroid and adrenal cortex), esophagus, endometrium, germ cells, head and neck, kidney, liver, lung, larynx and hypopharynx, mesothelioma, ovary, pancreas, prostate, rectum, renal, small intestine, soft tissue, testis, stomach, skin, ureter, vagina and vulva. Malignant neoplasias include inherited cancers exemplified by Retinoblastoma and Wilms tumor. In addition, malignant neoplasias include primary tumors in said organs and corresponding secondary tumors in distant organs ("tumor metastases"). Hematological tumors are exemplified by aggressive and indolent forms of leukemia and lymphoma, namely non-Hodgkins disease, chronic and acute myeloid leukemia (CML/AML), acute lymphoblastic leukemia (ALL), Hodgkins disease, multiple myeloma and T-cell lymphoma. Also included are myelodysplastic syndrome, plasma cell neoplasia, paraneoplastic syndromes, cancers of unknown primary site as well as AIDS-related malignancies. In a particular embodiment of the present invention, the cancer is kidney cancer, particularly renal cell carcinoma (RCC) which is also referred to as hypernephroma.

In a preferred embodiment of the present invention concentrations of sPRR in the sample of at least 5 ng/ml are indicative and/or predictive for pre-eclampsia, preferably concentrations of at least 10 n/ml.

In a further embodiment of the invention concentrations of sPRR in the sample of at least 3 µ/ml are indicative and/or predictive for a disease selected from the group comprising therapy refractory hypertension, hemolytic uremic syndrome, thrombotic microangiopathy, membranous glomerulonephritis, renal artery stenosis, hypertension and pre-eclampsia. In yet a further embodiment of the present invention concentrations of sPRR in the sample of at least 4 µ/ml are indicative and/or predictive for a disease selected from the group comprising thrombotic microangiopathy, membranous glomerulonephritis, renal artery stenosis, hypertension and pre-eclampsia. In yet a further embodiment of the present invention concentrations of sPRR in the sample of at least 5 µ/ml are indicative and/or predictive for a disease selected from the group comprising hypertension and pre-eclampsia.

The inventors found that the presence of sPRR in a sample of a subject is indicative and/or predictive for causes of secondary hypertension, e.g. therapy refractory hypertension, hemolytic uremic syndrome, thrombotic microangiopathy, membranous glomerulonephritis, and renal artery stenosis. Thus, in one embodiment of the present invention the presence of sPRR in a sample of a subject is indicative and/or predictive for therapy refractory hypertension, hemolytic uremic syndrome, thrombotic microangiopathy, membranous glomerulonephritis, and renal artery stenosis.

In a preferred embodiment of the present invention hypertension and/or early stage cardiovascular end-organ damage is selected from the group consisting of primary hypertension, secondary hypertension, severe hypertension, pulmonary hypertension, malignant hypertension, isolated systolic hypertension, Cushing's syndrome, hyperthyroidism, hypothyroidism, adrenal gland cancer, kidney disease, obesity/metabolic disorder, therapy refractory hypertension, hemolytic uremic syndrome, thrombotic microangiopathy, membranous glomerulonephritis, renal artery stenosis, ventricular failure, unstable angina, myocardiacinfarction, encephalopathy, pre-eclampsia, eclampsia, and cancer.

In a preferred embodiment of the present invention the presence of sPRR is determined by an immunoassay.

The diagnostic assay or assay or immunoassay can be of any type applied in the field of diagnostics, including but not restricted to assay methods based on enzymatic reactions, luminescence, fluorescence, and radio-chemicals.

In one embodiment of the present invention the immunoassay is selected from the group comprising immuno-precipitation, enzyme immunoassay (EIA), radio immunoassay (RIA) or fluorescent immunoassay, a chemiluminescent assay, an agglutination assay, nephelometric assay, turbidimetric assay, a Western blot, a competitive immunoassay, a noncompetitive immunoassay, a homogeneous immunoassay, a heterogeneous immunoassay, a bioassay and a reporter-assay such as a Luciferase-Assay. The preferred detection methods comprise strip tests, radio immunoassay, chemiluminescence- and fluorescence-immunoassay, Immunoblot assay, Enzyme-linked immunoassay (ELISA), Luminex-based bead arrays, and protein microarray assay.

The assay types can further be microtitre plate-based, chip-based, bead-based, wherein the biomarker proteins can be attached to the surface or in solution. The assays can be homogenous or heterogeneous assays, competitive and non-competitive assays. In a particularly preferred embodiment, the assay is in the form of a sandwich assay, which is a non-competitive immunoassay, wherein the molecule to be detected and/or quantified is bound to a first antibody and to a second antibody. The first antibody may be bound to a solid phase, e.g. a bead, a surface of a well or other container, a chip or a strip, and the second antibody is an antibody which is labeled, e.g. with a dye, with a radioisotope, or a reactive or catalytically active moiety. The amount of labeled antibody bound to the analyte is then measured by an appropriate method. The general composition and procedures involved with "sandwich assays" are well-established and known to the skilled person (The Immunoassay Handbook, Ed. David Wild, Elsevier LTD, Oxford; 3rd ed. (May 2005), ISBN-13: 978-0080445267; Hultschig C et al., Curr Opin Chem Biol. 2006 Feb.; 10(1):4-10. PMID: 16376134, incorporated herein by reference).

In the context of the present invention, "capture molecules" are molecules which may be used to bind target molecules or molecules of interest, i.e. analytes (i.e. in the context of the present invention the cardiovascular peptide(s)), from a sample. Capture molecules must, thus, be shaped adequately, both spatially and in terms of surface features, such as surface charge, hydrophobicity, hydrophilicity, presence or absence of lewis donors and/or acceptors, to specifically bind the target molecules or molecules of interest. Hereby, the binding may for instance be mediated by ionic, van-der-Waals, pi-pi, sigma-pi, hydrophobic or hydrogen bond interactions or a combination of two or more of the afore-mentioned interactions between the capture molecules and the target molecules or molecules of interest. In the context of the present invention, capture molecules may for instance be selected from the group comprising a nucleic acid molecule, a carbohydrate molecule, a PNA molecule, a protein, an antibody, a peptide or a glycoprotein. Preferably, the capture molecules are antibodies, including fragments thereof with sufficient affinity to a target or molecule of interest, and including recombinant antibodies or recombinant antibody fragments, as well as chemically and/or biochemically modified derivatives of said antibodies or fragments derived from the variant chain with a length of at least 12 amino acids thereof.

In a preferred embodiment the immunoassay is an ELISA.

The present invention also relates to the use of an anti-sPRR antibody or fragments thereof for the diagnosis of hypertension and/or cardiovascular end-organ damage.

Furthermore, encompassed is also the use of a research and/or diagnostic kit in the diagnosis of hypertension and/or early stage cardiovascular end-organ damage, wherein the kit comprises an anti-sPRR antibody or fragments thereof. In a preferred embodiment of the use of the anti-sPRR antibody or fragments thereof and/or the research and/or diagnostic kit the hypertension and/or cardiovascular end-organ damage is selected from the group of primary hypertension, secondary hypertension, severe hypertension, pulmonary hypertension, malignant hypertension, and isolated systolic hypertension, Cushing's syndrome, hyperthyroidism, hypothyroidism, adrenal gland cancer, kidney disease, obesity/metabolic disorder, therapy refractory hypertension, hemolytic uremic syndrome, thrombotic microangiopathy, membranous glomerulonephritis, renal artery stenosis, ventricular failure, unstable angina, myocardiacinfarction, encephalopathy, pre-eclampsia, eclampsia, and cancer.

Furthermore, encompassed is also the use of a research and/or diagnostic kit in the diagnosis of late stage cardiovascular end-organ damage for the diseases outlined above.

The invention relates in another aspect to a research and/or diagnostic kit for predicting the risk of a patient suffering from a primary disease or condition for contracting pulmonary arterial hypertension or for identifying a patient suffering from primary hypertension, secondary hypertension, severe hypertension, pulmonary hypertension, malignant hypertension, isolated systolic hypertension, Cushing's syndrome, hyperthyroidism, hypothyroidism, adrenal gland cancer, kidney disease, obesity/metabolic disorder, therapy refractory hypertension, hemolytic uremic syndrome, thrombotic microangiopathy, membranous glomerulonephritis, renal artery stenosis, ventricular failure, unstable angina, myocardiacinfarction, encephalopathy, pre-eclampsia, eclampsia, and cancer.

The immunological test kit according to the invention comprises the anti-sPRR antibody or a functional analog thereof or peptides or proteins of analogous function per se. The test kit of the invention comprises at least one complete anti-sPRR antibody or functionally analogous peptides or proteins of said receptor, optionally bound to a solid phase. Furthermore, the test kit may also comprise buffers, specific conjugate together with an enzyme, wash solution, substrate solution to detect the immune reaction and/or a quenching solution. Using these substances a person skilled in the art will be able to perform, e.g. an ELISA to detect sPRR. The buffers, specific conjugate plus enzyme, wash solution, substrate solution to detect immune reaction and quenching solution are well known to those skilled in the art. For example, it would be sufficient to have the test comprising a freeze-dried anti-sPRR antibody or peptides or proteins of anti-sPRR antibody analogous function and to add the buffers and other solutions immediately prior to testing the biological material. However, it is also possible to provide the test kit with the anti-sPRR antibody or its functionally analogous peptides of proteins bound to a solid phase. To detect sPRR, the specific conjugate, wash solution, substrate solution and quenching solution, which can be components of the test kit, have to be added according to a mode well known to those skilled in the art.

In another advantageous embodiment of the invention, it is envisioned that the test kit is a test strip comprising the anti-sPRR antibody or its functionally analogous peptides or proteins immobilized on a solid phase. For example, the test strip can be immersed in serum or other patient samples and incubated. Using a specific biochemical reaction on the test strip after formation of the sPRR/anti-sPRR antibody complex, a specific color reaction can be triggered by means of which sPRR can be detected.

The test system of the invention permits quantification of sPRR directly in a sample, e.g. in plasma or serum of patients. The detection method according to the invention is time saving and cost effective. Large amounts of the samples can be tested and, owing to the low amount of the equipment required, routine laboratories can be used.

The present invention also relates to the use of an inhibitor of the prorenin receptor and/or sPRR for the production of a medicament for the treatment of hypertension and/or cardiovascular end-organ damage. A preferred inhibitor of sPRR according to the present invention is a sPRR antibody according to the present invention.

Also enclosed herein is a method for detecting the presence of sPRR in a sample comprising the steps of: (a) capturing sPRR or fragments thereof comprised in said sample on a solid support; (b) contacting the captured sPRR with a labeled sPRR binding agent, (c) detecting the labeled sPRR binding agent.

In a preferred embodiment of the method for detecting the presence of sPRR the labeled sPRR binding agent is a labeled anti-sPRR antibody or a fragment thereof.

The present invention also relates to a sPRR antibody specifically binding to a polypeptide comprising the amino acid sequence of SEQ ID NO. 4. Furthermore, the present invention relates to a kit comprising a sPRR antibody according to the present invention. The kit is preferably an immunological test kit. Also enclosed herein is the use of an antibody or a kit according to the present invention in a method according to the present invention. Furthermore the present invention relates to the use of an antibody or a kit according to the present invention in an immunoassay.

The "sPRR antibody" or "anti-sPRR antibody" in the meaning of the invention binds the sPRR in a specific fashion. Even though the antibody binds sPRR in a specific fashion, it will be understood by those skilled in the art that the antibody may also bind the intact receptor (prorenin receptor RPP). The antibody can also be modified (e.g. oligomeric, reduced, oxidized and labeled antibodies). The terms "anti-sPRR antibody" or "antibody" as used herein comprise both intact molecules and also antibody fragments such as Fab, F(ab')$_2$ and Fv capable of binding specific epitope determinance of the sPRR, preferably SEQ ID NO. 4. In these fragments the sPRR antibody(ies) capability of selectively binding its antigen or receptor is retained in part, the fragments being defined as follows: (1) Fab, the fragment which contains a monovalent antigen-binding fragment of an antibody molecule, can be generated by cleavage of a whole antibody using the enzyme papaine, thereby obtaining an intact light chain and part of a heavy chain; (2) the Fab fragment of an antibody molecule can be produced by treatment of a whole antibody with pepsin and subsequent reduction, thereby obtaining an intact light chain and part of a heavy chain, two Fab fragments per antibody molecule are obtained; (3) F(ab')$_2$ the fragment of the antibody which can be obtained by treatment of a whole antibody with the enzyme pepsin without subsequent reduction, F(ab')$_2$ is a dimer comprised of two Fab fragments held together by two disulfate bonds; (4) Fv defined as fragment modified by genetic engineering which includes the variable region of the light chain and the variable region of the heavy chain and is expressed in the form of two chains; and (5) single-chain antibody (SCA) defined as a molecule modified by genetic engineering, which includes the variable region of the light chain and the variable region of the heavy chain, linked by a suitable polypeptide linker to perform a genetically fused single-chain molecule. In a preferred embodiment of the present invention sPRR is captured by a polyclonal anti-sPRR antibody bound to a solid surface and the labeled sPRR binding agent is a labeled polyclonal anti-sPRR antibody, preferably labeled with horseradish peroxidase (HRP).

The term "epitope" as used in the present invention represents any antigen determinant on the sPRR. Epitope determinance nomially consists of chemically active surface groups of molecules such as amino acids or sugar-side chains and normally has specific features of the three dimensional structure as well as specific chart properties.

An "immune reaction" in the meaning of the invention is a specific interaction between the sPRR or peptides or proteins of analogous function and anti-sPRR antibodies. The immune reaction can be detected using various immunoassays. In this context the term "specific binding" refers to antibodies raised against the molecule of interest or a fragment thereof. An antibody is considered to be specific if its affinity towards the molecule of interest or the afore-mentioned fragment thereof is at least 50-fold higher, preferably 100-fold higher, more preferably at least 1,000-fold higher than towards other molecules comprised in a sample containing the molecule of interest. It is well known in the art how to make antibodies and to select antibodies with a given specificity.

"Immunoassays" in the meaning of the invention are assays utilizing the specific interaction between the sPRR and the anti-sPRR antibodies or fragments thereof, in order to detect the presence or determine the concentration of sPRR. For example, a detection in quantification of sPRR can be performed with the aid of said antibodies or fragments thereof, e.g. by immuno-precipitation or immuno-blotting.

In a preferred embodiment of the present invention the labeled anti-sPRR antibody or fragments thereof is labeled with a label selected from the group consisting of peroxidases, alkaline phosphatises, glucose oxidase, and horseradish peroxidase (HRP).

In a preferred embodiment of the invention sPRR is captured by an anti-sPRR antibody bound to said solid support. The skilled artisan knows ways and methods to bind antibodies to a solid support, e.g. a microtiter plate.

"Patients" or "subjects" are used interchangeable herein and in the meaning of the invention are understood to be all persons, irrespective whether or not they exhibit pathological changes, unless stated otherwise. In the meaning of the invention, any sample collected from cells, tissues, organs or the like can be a sample of a patient to be diagnosed. In one embodiment subjects are human or non-human animals, preferably mammals. In a preferred embodiment the patient according to the invention is a human. In a further preferred embodiment of the invention the patient is a human suspected to have hypertension and/or a cardiovascular end-organ damage.

It will be apparent that the methods of the present invention, as well as the sPRR antibodies, kits and uses as substantially described herein or illustrated in the description and the examples, are also subject of the present invention and claimed herewith. In this respect, it is also understood that the embodiments as described in the description and/or any one of the examples, can be independently used and combined with any one of the embodiments described herein before and claimed in the appended claims set. Thus, these and other embodiments are disclosed and encompassed by the description and examples of the present invention.

TABLE 1

Sequences used herein

| SEQ ID NO. | Amino acid sequence | Notation |
|---|---|---|
| 1 | MAVFVVLLAL VAGVLGNEFS ILKSPGSVVF RNGNWPIPGE RIPDVAALSM GFSVKEDLSW PGLAVGNLFH RPRATVMVMV KGVNKLALPP GSVISYPLEN AVPFSLDSVA NSIHSLFSEE TPVVLQLAPS EERVYMVGKA NSVFEDLSVT LRQLRNRLFQ ENSVLSSLPL NSLSRNNEVD LLFLSELQVL HDISSLLSRH KHLAKDHSPD LYSLELAGLD EIGKRYGEDS EQFRDASKIL VDALQKFADD MYSLYGGNAV VELVTVKSFD TSLIRKTRTI LEAKQAKNPA SPYNLAYKYN FEYSVVFNMV LWIMIALALA VIITSYNIWN MDPGYDSIIY RMTNQKIRMD | Pro-renin receptor (full-length) |

TABLE 1 -continued

Sequences used herein

| SEQ ID NO. | Amino acid sequence | Notation |
|---|---|---|
| 2 | MAVFVVLLAL VAGVLGNEFS ILKSPGSVVF RNGNWPIPGE RIPDVAALSM GFSVKEDLSW PGLAVGNLFH RPRATVMVMV KGVNKLALPP GSVISYPLEN AVPFSLDSVA NSIHSLFSEE TPVVLQLAPS EERVYMVGKA NSVFEDLSVT LRQLRNRLFQ ENSVLSSLPL NSLSRNNEVD LLFLSELQVL HDISSLLSRH KHLAKDHSPD LYSLELAGLD EIGKRYGEDS EQFRDASKIL VDALQKFADD MYSLYGGNAV VELVTVKSFD TSLIRKTRTI LEAKQAKNPA SPYNLAYKYN FE | Soluble pro-renin receptor (extracellular part of pro-reinin receptor; amino acids 1 to 202 of pro-reinin receptor) |
| 3 | MAVFVVLLAL VAGVLGNEFS ILKSPGSVVF RNGNWPIPGE RIPDVAALSM GFSVKEDLSW PGLAVGNLFH RPRATVMVMV KGVNKLALPP GSVISYPLEN AVPFSLDSVA NSIHSLFSEE TPVVLQLAPS EERVYMVGKA NSVFEDLSVT LRQLRNRLFQ ENSVLSSLPL NSLSRNNEVD LLFLSELQVL HDISSLLSRH KHLAKDHSPD LYSLELAGLD EIGKRYGEDS EQFRDASKIL VDALQKFADD MYSLYGGNAV VELVTVKSFD TSLIRKT | |
| 4 | AVPFSLDSVA NSIHSLFSEE TPVVLQLAPS EERVYMVGKA NSVFEDLSVT LRQLRNRLFQ ENSVLSSLPL NSLSRNNEVD LLFLSELQVL HDISSLLSRH KHLAKDHSPD LYSLELAGLD EIGKRYGEDS EQFRDASKIL VDALQKFADD MYSLYGG | Antigen of the antibodies used in the examples (amino acids 101 to 257 of sPRR) |

FIGURE LEGENDS

FIG. 1: Sequence of pro-renin receptor. The extracellular part of the receptor is underlined (sPRR; SEQ ID NO. 2). The sPRR fragment starting from amino acid 1 until the proteolytic cleavage site after amino acid 277 (SEQ ID NO. 3) is in bold letters. The transmembrane region of the PRR is in italic.

FIG. 2: sPRR concentrations in different groups of patients.

Figure 3:
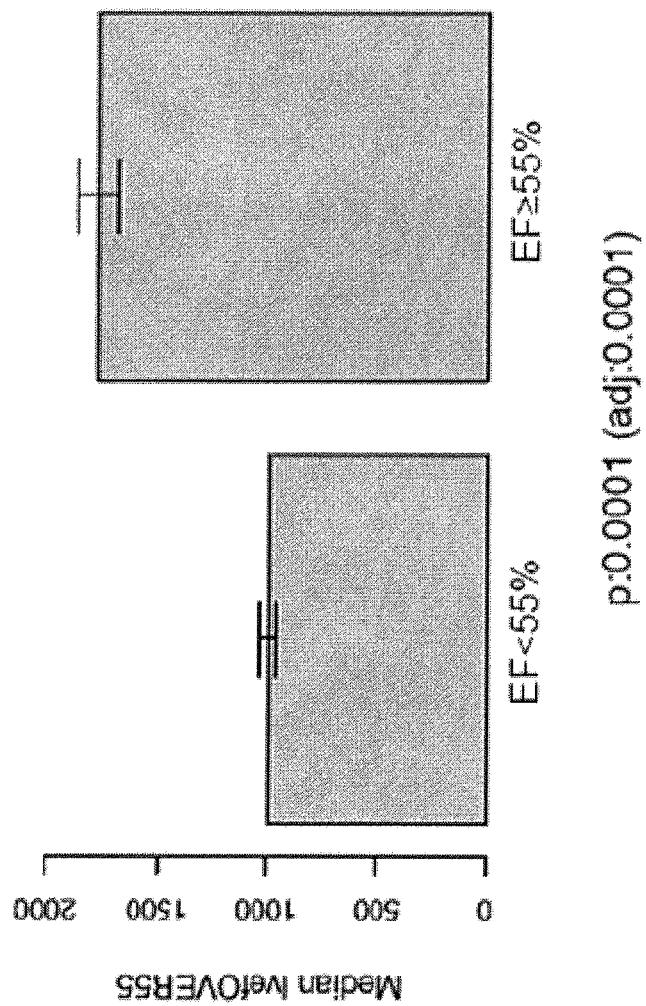

FIG. 3: shows sPRR is significantly lowered in systolic heart insufficiency

Figure 4:
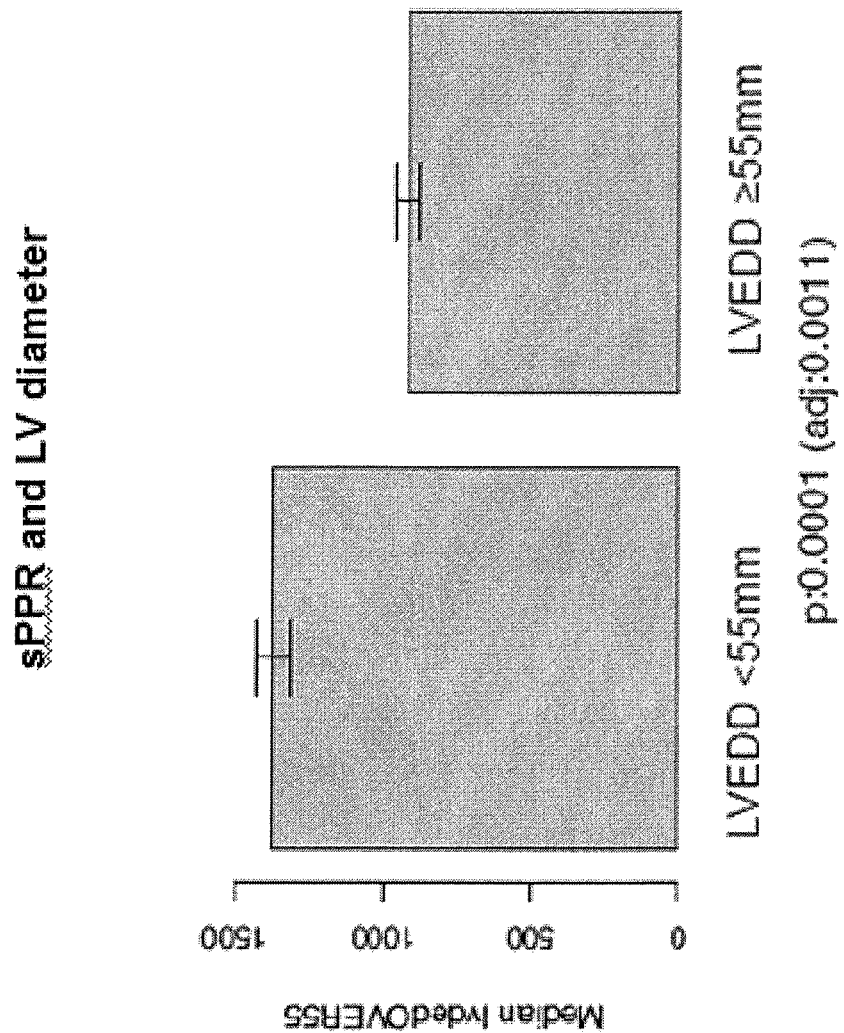

FIG. 4: shows sPRR is significantly lowered in cases of enlarged left ventricle (dilative cardiomyopathy).

Figure 5:
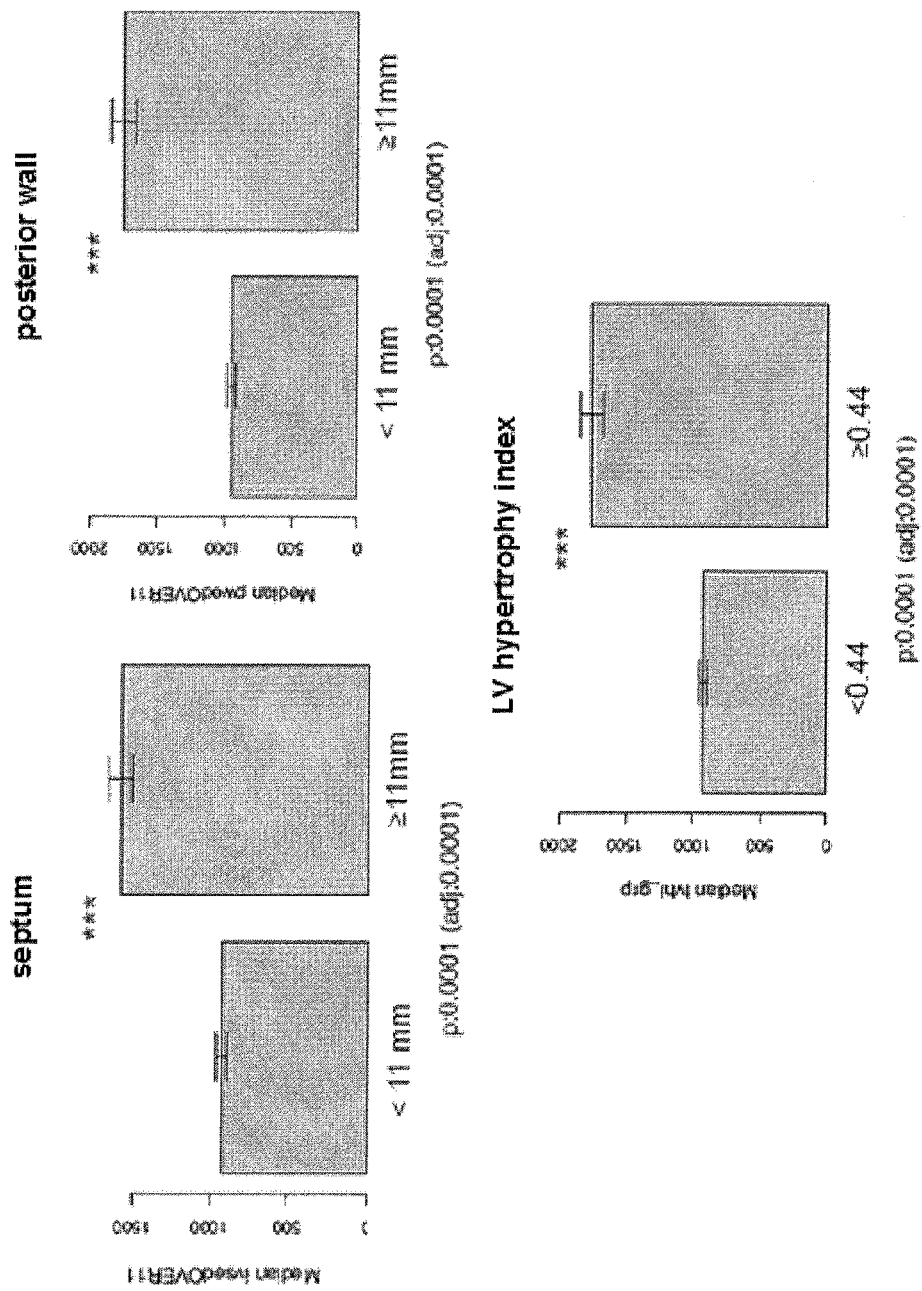

FIG. 5: shows sPRR is elevated in cases of hypertrophic obstructive cardiomyopathy.

Figure 6:
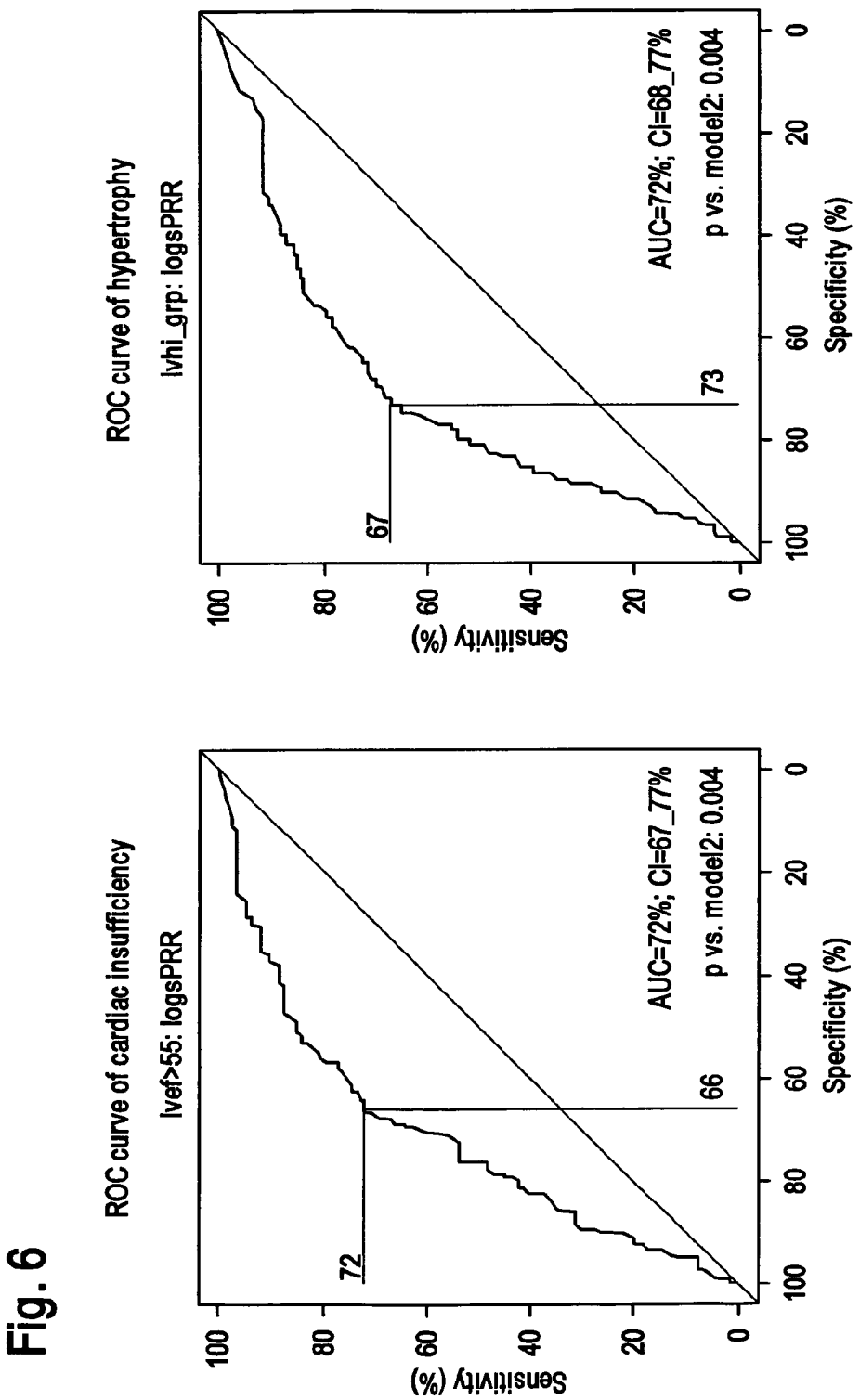

FIG. 6: shows the sensitivity and specificity for detecting heart insufficiency and cardiac hypertrophy for sPRR (ROC curve).

Figure 7:
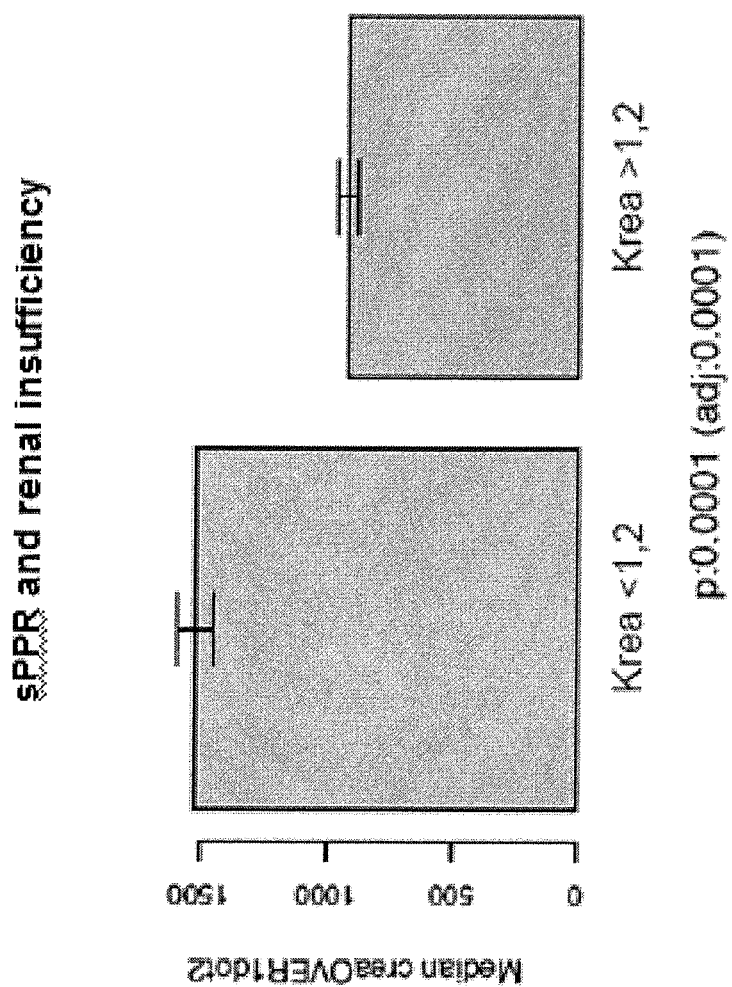

FIG. 7: shows sPRR is lowered in cases of kidney insufficiency.

Figure 8:
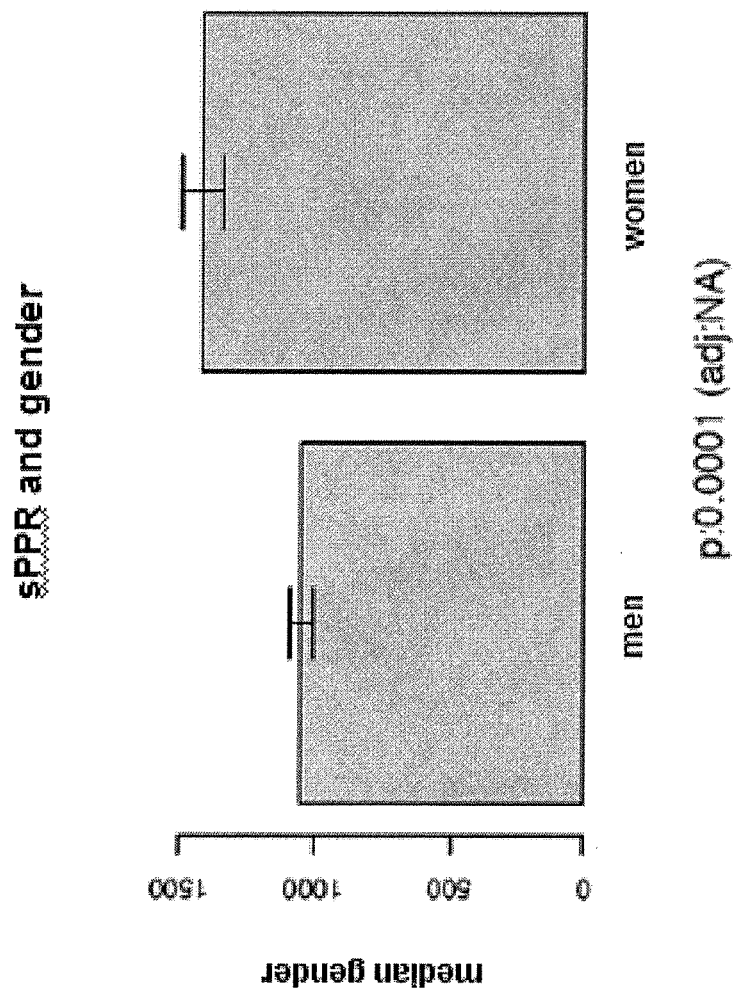

FIG. 8: shows sPRR is lower in male patients (gender effect).

Figure 9:
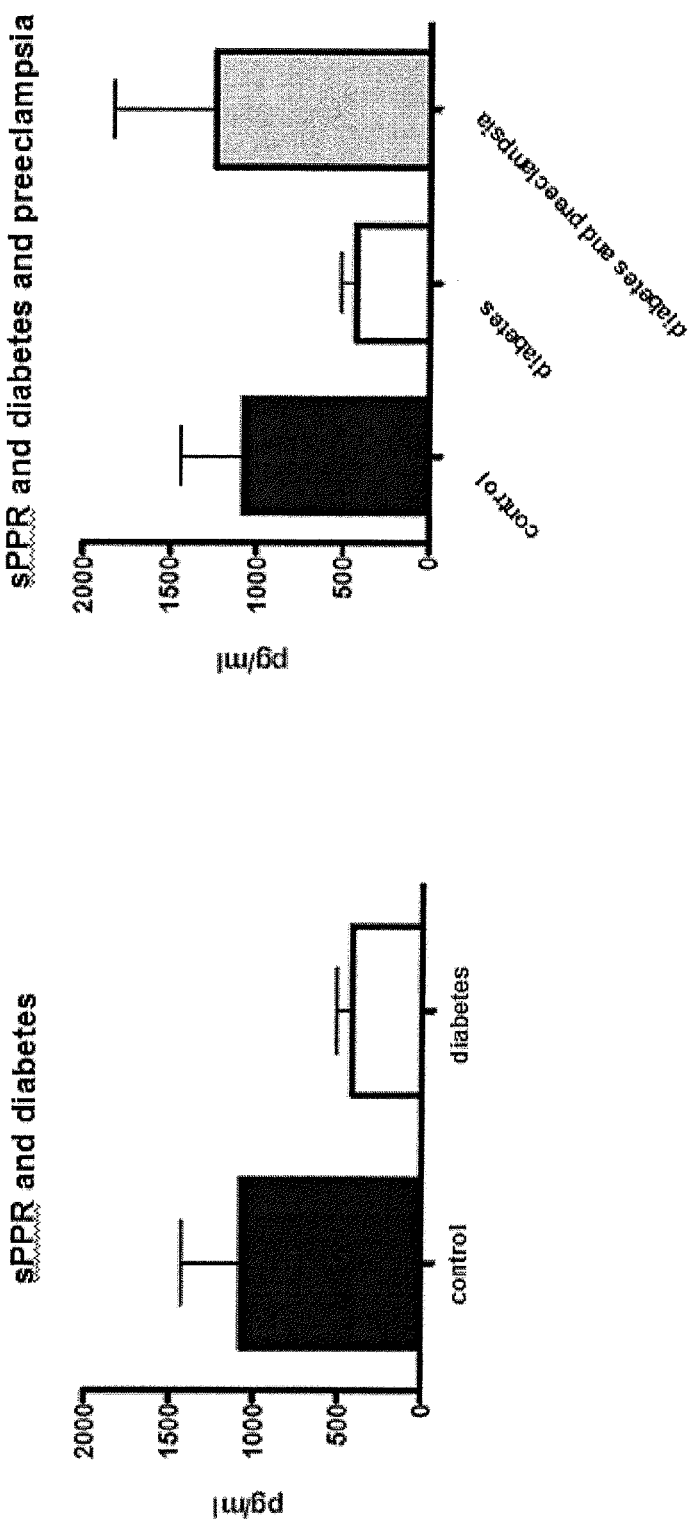

FIG. 9: shows sPRR is lower in female patients that are pregnant and have diabetes.

Figure 10:
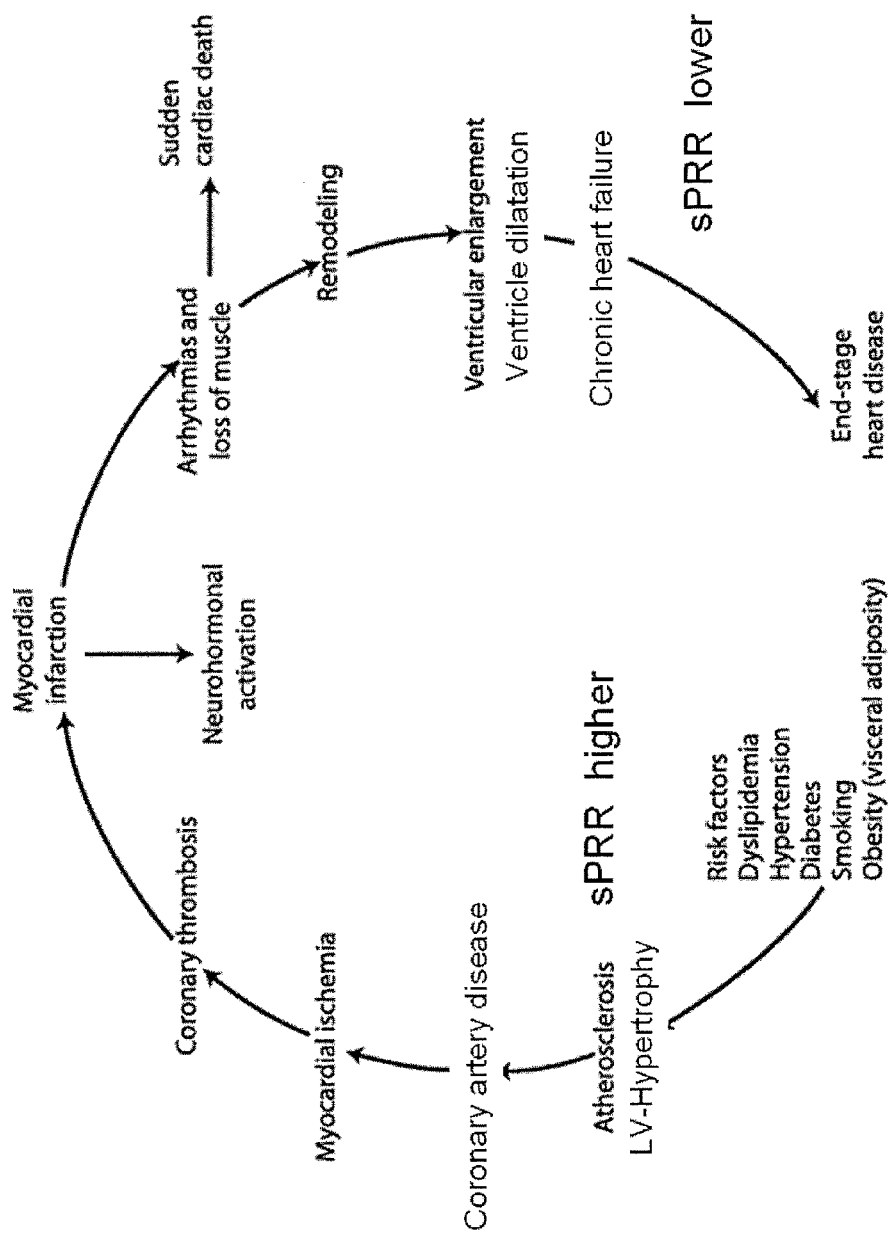

FIG. 10: shows the disease states of the CVD continuum.

EXAMPLE 1

Production of sPRR Antibody

Production of the sPRR antibody was performed by immunization of rabbits with a polypeptide having the sequence according to SEQ ID NO. 4. After bleeding of the rabbits the antiserum containing polyclonal antibodies was isolated.

Sample Collection and Handling:

Venous blood samples are collected aseptically. Serum is suitable for use in the assay. EDTA, or citrated plasma, cultured cell extracts or cell culture supernatant can also be used. Remove the serum or plasma from the clot or red cells. Freeze-thaw cycles should be avoided.

Detection of sPRR in Samples of Patients

The sPRR as detected by a solid phase sandwich sPRR-ELISA. Therefore a fraction of the sPRR antibody is immobilised on a microtiter plate to create the solid phase. Another portion of the sPRR antibody is labelled with horseradish peroxidise (HRP). Serum or plasma samples derived from patients suffering from the diseases indicated in FIG. 2 and Table 2 (control group: normal donors) or standards are diluted 1:25 fold in PBS-Casein buffer and applied to the solid phase. Non-specific biding is blocked by a blocking buffer. After a washing step the HRP-labelled sPRR antibody was added. The substrate for HRP is added. The reaction between HRP and substrate results in colour development. The colour intensity is proportional to the amount of sPRR present in samples and standards. The amount of sPRR can be quantitated by measuring absorbance using an ELISA plate reader. The average concentrations for each patient group are given in FIG. 2 and Table 2. Each patient group comprises about 50 patients.

TABLE 2

| Patient group | ng/ml sPRR (aa 101-257; SEQ ID NO. 4) mean | Standard deviation |
|---|---|---|
| Normal donors | 2.813 | 1.885 |
| Therapy refractory hypertensive patients | 3.748 | 7.136 |
| Hemolytic uremic syndrome | 3.947 | 4.933 |

TABLE 2-continued

| Patient group | ng/ml sPRR (aa 101-257; SEQ ID NO. 4) mean | Standard deviation |
|---|---|---|
| Thrombotic microangiopathy | 4.760 | 8.634 |
| Membranous glomerulonephritis | 4.622 | 5.127 |
| Renal artery stenosis | 5.236 | 4.597 |
| Hypertensive patients | 5.616 | 1.449 |
| Normal pregnancies | 4.700 | 3.854 |
| Preeclampsia | 11.030 | 7.760 |

EXAMPLE 2

The experiments were performed in accordance with the experimental procedure outlined in example 1.

sPRR is Significantly Lowered in Systolic Heart Insufficiency (or Systolic Heart Failure); See FIG. 3 total: n=569 patients: median (quantile): 1164 (653/1715)

EF<55: 454 patients: median (quantile): 997 (579/1715)

EF>55: 115 patients: median(quantile): 1775 (1257/1715)

(EF=ejection fraction normal value: >55%); see FIG. 3 sPRR is highly significant also if adjusted for age and gender.

sPRR is Significantly Lowered in Cases of Enlarged Left Ventricle (Dilative Cardiomyopathy); See FIG. 4 total: n=565 patients: median (quantile): 1163 (649/2348)

LVEDD<55: 288 patients: median (quantile): 1374 (800/2348)

EF>55: 277 patients: median (quantile): 928 (571/2348)

LVEDD=enddiastolic diameter of the left ventricle; normal value=<55 mm; see FIG. 4 sPRR is highly significant also if adjusted for age and gender.

sPRR is Elevated in Cases of Hypertrophic Obstructive Cardiomyopathy; See FIG. 5

Number of patients

|  | total | with hypertrophy | without hypertrophy |
|---|---|---|---|
| septum > 11 mm | 566 | 319 | 247 |
| back wall > 11 mm | 564 | 396 | 168 |
| LV hypertrophy index | 563 | 380 | 183 |
| septum > 11 mm | 1160 (650/1490) | 924 (537/1490) | 1586 (926/1490)*** |
| back wall > 11 mm | 1160 (651/1599) | 948 (557/1599) | 1753 (1156/1599)*** |
| LV hypertrophy index | 1163 (651/1544) | 924 (543/1544) | 1769 (1156/1544)*** |

Normal value: thickness of septum: <11 mm, back wall thickness<11 mm, LV hypertrophy index: <0.44 sPRR is highly significant also if adjusted for age and gender.

FIG. 6 shows the sensitivity and specificity for detecting heart insufficiency and cardiac hypertrophy for sPRR (ROC curve).

sPRR is Lowered in Cases of Kidney Insufficiency (Also Renal Insufficiency); See FIG. 7

|  | total | kidney insufficiency | no kidney insufficiency |
|---|---|---|---|
| Krea 1, 2 | 544 | 239 | 305 |
| Krea 1, 2 | 1156 (649/2552) | 1520 (896/2552) | 925 (528/2552)*** |

Normal value: kreatinin in serum: <1,2 mg/dl sPRR is highly significant also if adjusted for age and gender.

sPRR is Lower in Male Patients (Gender Effect); See FIG. 8

|  | total | male | female |
|---|---|---|---|
| gender | 574 | 376 | 198 |
| gender | 1160 (650/1710) | 1049 (583/1710) | 1418 (809/1710)*** | sPRR is highly significant also if adjusted for age and gender.

sPRR is Lower in Female Patients that are Pregnant and Have Diabetes; See FIG. 9

Number of patients:

Healthy females n=3

Trimenon n=51

Diabetes n=96 (Typ 1=37, Typ 2=10, gestation diabetes n=49)

Healthy pregnant median (quantile): 262,1 (126,7/748), arithmetic average+SEM: 1077±358

Diabetes median (quantile): 112,5 (97,8/352,7)

arithmetic average+SEM: 423,4±94,3

Diabetes+pre-eclampsia median (quantile):465,3 (97,8/1040)

arithmetic average: 1242±584,7

Further quantification of further groups

|  | C | DM1 | DM2 | GDM | DPE |
|---|---|---|---|---|---|
| n = 239 | n = 51 | n = 37 | n = 10 | n = 49 | n = 11 |
| Soluble prorenin receptor concentration | 262 (146-441) | 119 (98-160) .002* | 107 (98-272) .02* | 104 (98-188) .002* | 465 (98-3540) .8 | sPRR is Elevated in Diabetes and Pre-Eclampsia: See FIG. 9

The invention claimed is:

1. An in vitro method for diagnosis or prediction of hypertension and/or early-stage cardiovascular end-organ damage in a patient, the method comprising determining the concentration of soluble prorenin receptor (sPRR) in a sample from the patient using an antibody or antibody fragment that immunologically binds a polypeptide comprising SEQ ID NO:4 wherein the presence of the polypeptide at increased concentration compared to the concentration of such a polypeptide in samples from healthy subjects is indicative for hypertension and/or early-stage cardiovascular end-organ damage and wherein the presence of the polypeptide at decreased concentration compared to the concentration of such a polypeptide in samples from healthy subjects is indicative for late stage cardiovascular end-organ damage.

2. The in vitro method according to claim 1, wherein the presence of said polypeptide at a concentration of at least 3 ng/ml is indicative of the hypertension and/or early-stage cardiovascular end-organ disease.

3. The method according to claim 2, wherein the presence of said polypeptide at a concentration of at least 4 ng/ml is indicative of the hypertension and/or early-stage cardiovascular end-organ disease.

4. The method according to claim 2, wherein the presence of said polypeptide at a concentration of at least 5 ng/ml is indicative of the hypertension and/or early-stage cardiovascular end-organ disease.

5. The method according to claim 2, wherein the presence of said polypeptide at a concentration of at least 10 ng/ml is indicative of the hypertension and/or early-stage cardiovascular end-organ disease.

6. The in vitro method according to claim 1, wherein the sample is selected from the group comprising a blood sample, a serum sample, and a plasma sample.

7. The in vitro method according to claim 1, wherein the immunoassay is selected from the group of an immuno-precipitation assay, an enzyme immunoassay (EIA), a radioimmunoassay (RIA) or a fluorescent immunoassay, a chemiluminescent assay, an agglutination assay, a nephelometric assay, a turbidimetric assay, a Western blot, a competitive immunoassay, a noncompetitive immunoassay, a homogeneous immunoassay, a heterogeneous immunoassay, a bioassay and a reporter-assay such as a Luciferase-Assay.

8. The in vitro method according to claim 1, wherein the immunoassay is an enzyme-linked immunosorbent assay (ELISA).

9. An in vitro method for determining the concentration of soluble prorenin receptor (sPRR) in a sample from a patient suspected of developing hypertension and/or early stage cardiovascular end-organ disease, the method comprising conducting an immunoassay that determines the level of a polypeptide comprising SEQ ID NO:2, SEQ ID NO:3 or SEQ ID NO:4 in such a sample.

10. The in vitro method according to claim 9, wherein the concentration of the polypeptide is determined to be at least 3 ng/ml.

11. The in vitro method according to claim 10, wherein the concentration of the polypeptide is determined to be at least 4 ng/ml.

12. The in vitro method according to claim 11, wherein the concentration of the polypeptide is determined to be at least 5 ng/ml.

13. The in vitro method according to claim 9, wherein the sample is selected from the group comprising a blood sample, a serum sample, and a plasma sample.

14. The in vitro method according to claim 9, wherein the immunoassay is selected from the group of an immuno-precipitation assay, an enzyme immunoassay (EIA), a radioimmunoas say (RIA) or a fluorescent immunoassay, a chemiluminescent assay, an agglutination assay, a nephelometric assay, a turbidimetric assay, a Western blot, a competitive immunoassay, a noncompetitive immunoassay, a homogeneous immunoassay, a heterogeneous immunoassay, a bioassay and a reporter-assay such as a Luciferase-Assay.

15. The in vitro method according to claim 14, wherein the immunoassay is an ELISA.

16. The in vitro method according to claim 9, wherein the immunoassay determines the level of a polypeptide comprising SEQ ID NO:2 is such a sample.

17. The in vitro method according to claim 9, wherein the immunoassay determines the level of a polypeptide comprising SEQ ID NO:3 is such a sample.

18. The in vitro method according to claim 9, wherein the immunoassay determines the level of a polypeptide comprising SEQ ID NO:4 is such a sample.

* * * * *

UNITED STATES PATENT AND TRADEMARK OFFICE
CERTIFICATE OF CORRECTION

PATENT NO.        : 8,846,324 B2
APPLICATION NO.   : 13/878244
DATED             : September 30, 2014
INVENTOR(S)       : Harald Heidecke et al.

It is certified that error appears in the above-identified patent and that said Letters Patent is hereby corrected as shown below:

In the Claims

In claim 9, column 26, line 15, delete "early stage" and insert --early-stage-- therefor.

In claim 14, column 26, lines 34-35, delete "radioimmunoas say" and insert --radioimmunoassay-- therefor.

In claim 16, column 26, line 45, delete "is" and insert --in-- therefor.

In claim 17, column 26, line 48, delete "is" and insert --in-- therefor.

In claim 18, column 26, line 51, delete "is" and insert --in-- therefor.

Signed and Sealed this
Thirtieth Day of December, 2014

Michelle K. Lee
*Deputy Director of the United States Patent and Trademark Office*

SEQUENCE LISTING

<160> NUMBER OF SEQ ID NOS: 4

<210> SEQ ID NO 1
<211> LENGTH: 350
<212> TYPE: PRT
<213> ORGANISM: Homo sapiens

<400> SEQUENCE: 1

```
Met Ala Val Phe Val Leu Leu Ala Leu Val Ala Gly Val Leu Gly
  1               5                  10                  15

Asn Glu Phe Ser Ile Leu Lys Ser Pro Gly Ser Val Val Phe Arg Asn
                 20                  25                  30

Gly Asn Trp Pro Ile Pro Gly Glu Arg Ile Pro Asp Val Ala Ala Leu
             35                  40                  45

Ser Met Gly Phe Ser Val Lys Glu Asp Leu Ser Trp Pro Gly Leu Ala
 50                  55                  60

Val Gly Asn Leu Phe His Arg Pro Arg Ala Thr Val Met Val Met Val
 65                  70                  75                  80

Lys Gly Val Asn Lys Leu Ala Leu Pro Pro Gly Ser Val Ile Ser Tyr
                 85                  90                  95

Pro Leu Glu Asn Ala Val Pro Phe Ser Leu Asp Ser Val Ala Asn Ser
                100                 105                 110

Ile His Ser Leu Phe Ser Glu Thr Pro Val Val Leu Gln Leu Ala
                115                 120                 125

Pro Ser Glu Glu Arg Val Tyr Met Val Gly Lys Ala Asn Ser Val Phe
            130                 135                 140

Glu Asp Leu Ser Val Thr Leu Arg Gln Leu Arg Asn Arg Leu Phe Gln
145                 150                 155                 160

Glu Asn Ser Val Leu Ser Ser Leu Pro Leu Asn Ser Leu Ser Arg Asn
                165                 170                 175

Asn Glu Val Asp Leu Leu Phe Leu Ser Glu Leu Gln Val Leu His Asp
                180                 185                 190

Ile Ser Ser Leu Leu Ser Arg His Lys His Leu Ala Lys Asp His Ser
            195                 200                 205

Pro Asp Leu Tyr Ser Leu Glu Leu Ala Gly Leu Asp Glu Ile Gly Lys
210                 215                 220

Arg Tyr Gly Glu Asp Ser Glu Gln Phe Arg Asp Ala Ser Lys Ile Leu
225                 230                 235                 240

Val Asp Ala Leu Gln Lys Phe Ala Asp Asp Met Tyr Ser Leu Tyr Gly
                245                 250                 255

Gly Asn Ala Val Val Glu Leu Val Thr Val Lys Ser Phe Asp Thr Ser
            260                 265                 270

Leu Ile Arg Lys Thr Arg Thr Ile Leu Glu Ala Lys Gln Ala Lys Asn
275                 280                 285

Pro Ala Ser Pro Tyr Asn Leu Ala Tyr Lys Tyr Asn Phe Glu Tyr Ser
            290                 295                 300

Val Val Phe Asn Met Val Leu Trp Ile Met Ile Ala Leu Ala Leu Ala
305                 310                 315                 320

Val Ile Ile Thr Ser Tyr Asn Ile Trp Asn Met Asp Pro Gly Tyr Asp
                325                 330                 335

Ser Ile Ile Tyr Arg Met Thr Asn Gln Lys Ile Arg Met Asp
            340                 345                 350
```

<210> SEQ ID NO 2
<211> LENGTH: 302

<212> TYPE: PRT
<213> ORGANISM: Homo sapiens

<400> SEQUENCE: 2

Met Ala Val Phe Val Val Leu Leu Ala Leu Val Ala Gly Val Leu Gly
1               5                   10                  15

Asn Glu Phe Ser Ile Leu Lys Ser Pro Gly Ser Val Val Phe Arg Asn
            20                  25                  30

Gly Asn Trp Pro Ile Pro Gly Glu Arg Ile Pro Asp Val Ala Ala Leu
        35                  40                  45

Ser Met Gly Phe Ser Val Lys Glu Asp Leu Ser Trp Pro Gly Leu Ala
    50                  55                  60

Val Gly Asn Leu Phe His Arg Pro Arg Ala Thr Val Met Val Met Val
65                  70                  75                  80

Lys Gly Val Asn Lys Leu Ala Leu Pro Pro Gly Ser Val Ile Ser Tyr
                85                  90                  95

Pro Leu Glu Asn Ala Val Pro Phe Ser Leu Asp Ser Val Ala Asn Ser
            100                 105                 110

Ile His Ser Leu Phe Ser Glu Glu Thr Pro Val Val Leu Gln Leu Ala
        115                 120                 125

Pro Ser Glu Glu Arg Val Tyr Met Val Gly Lys Ala Asn Ser Val Phe
    130                 135                 140

Glu Asp Leu Ser Val Thr Leu Arg Gln Leu Arg Asn Arg Leu Phe Gln
145                 150                 155                 160

Glu Asn Ser Val Leu Ser Ser Leu Pro Leu Asn Ser Leu Ser Arg Asn
                165                 170                 175

Asn Glu Val Asp Leu Leu Phe Leu Ser Glu Leu Gln Val Leu His Asp
            180                 185                 190

Ile Ser Ser Leu Leu Ser Arg His Lys His Leu Ala Lys Asp His Ser
        195                 200                 205

Pro Asp Leu Tyr Ser Leu Glu Leu Ala Gly Leu Asp Glu Ile Gly Lys
    210                 215                 220

Arg Tyr Gly Glu Asp Ser Glu Gln Phe Arg Asp Ala Ser Lys Ile Leu
225                 230                 235                 240

Val Asp Ala Leu Gln Lys Phe Ala Asp Asp Met Tyr Ser Leu Tyr Gly
                245                 250                 255

Gly Asn Ala Val Val Glu Leu Val Thr Val Lys Ser Phe Asp Thr Ser
            260                 265                 270

Leu Ile Arg Lys Thr Arg Thr Ile Leu Glu Ala Lys Gln Ala Lys Asn
        275                 280                 285

Pro Ala Ser Pro Tyr Asn Leu Ala Tyr Lys Tyr Asn Phe Glu
    290                 295                 300

<210> SEQ ID NO 3
<211> LENGTH: 277
<212> TYPE: PRT
<213> ORGANISM: Homo sapiens

<400> SEQUENCE: 3

Met Ala Val Phe Val Val Leu Leu Ala Leu Val Ala Gly Val Leu Gly
1               5                   10                  15

Asn Glu Phe Ser Ile Leu Lys Ser Pro Gly Ser Val Val Phe Arg Asn
            20                  25                  30

Gly Asn Trp Pro Ile Pro Gly Glu Arg Ile Pro Asp Val Ala Ala Leu
        35                  40                  45

```
Ser Met Gly Phe Ser Val Lys Glu Asp Leu Ser Trp Pro Gly Leu Ala
    50                  55                  60

Val Gly Asn Leu Phe His Arg Pro Arg Ala Thr Val Met Val Met Val
65                  70                  75                  80

Lys Gly Val Asn Lys Leu Ala Leu Pro Pro Gly Ser Val Ile Ser Tyr
                85                  90                  95

Pro Leu Glu Asn Ala Val Pro Phe Ser Leu Asp Ser Val Ala Asn Ser
                100                 105                 110

Ile His Ser Leu Phe Ser Glu Glu Thr Pro Val Val Leu Gln Leu Ala
                115                 120                 125

Pro Ser Glu Glu Arg Val Tyr Met Val Gly Lys Ala Asn Ser Val Phe
130                 135                 140

Glu Asp Leu Ser Val Thr Leu Arg Gln Leu Arg Asn Arg Leu Phe Gln
145                 150                 155                 160

Glu Asn Ser Val Leu Ser Ser Leu Pro Leu Asn Ser Leu Ser Arg Asn
                165                 170                 175

Asn Glu Val Asp Leu Leu Phe Leu Ser Glu Leu Gln Val Leu His Asp
                180                 185                 190

Ile Ser Ser Leu Leu Ser Arg His Lys His Leu Ala Lys Asp His Ser
                195                 200                 205

Pro Asp Leu Tyr Ser Leu Glu Leu Ala Gly Leu Asp Glu Ile Gly Lys
210                 215                 220

Arg Tyr Gly Glu Asp Ser Glu Gln Phe Arg Asp Ala Ser Lys Ile Leu
225                 230                 235                 240

Val Asp Ala Leu Gln Lys Phe Ala Asp Asp Met Tyr Ser Leu Tyr Gly
                245                 250                 255

Gly Asn Ala Val Val Glu Leu Val Thr Val Lys Ser Phe Asp Thr Ser
                260                 265                 270

Leu Ile Arg Lys Thr
                275

<210> SEQ ID NO 4
<211> LENGTH: 157
<212> TYPE: PRT
<213> ORGANISM: Artificial Sequence
<220> FEATURE:
<223> OTHER INFORMATION: Epitope/antigen for sPRR antibodies (amino
      acids 101 to 257 of full length sPRR)

<400> SEQUENCE: 4

Ala Val Pro Phe Ser Leu Asp Ser Val Ala Asn Ser Ile His Ser Leu
1               5                   10                  15

Phe Ser Glu Glu Thr Pro Val Val Leu Gln Leu Ala Pro Ser Glu Glu
                20                  25                  30

Arg Val Tyr Met Val Gly Lys Ala Asn Ser Val Phe Glu Asp Leu Ser
                35                  40                  45

Val Thr Leu Arg Gln Leu Arg Asn Arg Leu Phe Gln Glu Asn Ser Val
                50                  55                  60

Leu Ser Ser Leu Pro Leu Asn Ser Leu Ser Arg Asn Asn Glu Val Asp
65                  70                  75                  80

Leu Leu Phe Leu Ser Glu Leu Gln Val Leu His Asp Ile Ser Ser Leu
                85                  90                  95

Leu Ser Arg His Lys His Leu Ala Lys Asp His Ser Pro Asp Leu Tyr
                100                 105                 110

Ser Leu Glu Leu Ala Gly Leu Asp Glu Ile Gly Lys Arg Tyr Gly Glu
                115                 120                 125
```

```
Asp Ser Glu Gln Phe Arg Asp Ala Ser Lys Ile Leu Val Asp Ala Leu
    130                 135                 140

Gln Lys Phe Ala Asp Asp Met Tyr Ser Leu Tyr Gly Gly
145                 150                 155
```